United States Patent [19]

Sandri et al.

[11] 4,319,032

[45] Mar. 9, 1982

[54] DERIVATIVES OF AMINOALKYL ALKYLENE UREAS

[75] Inventors: Joseph M. Sandri, Arnold; John W. Calentine, Pasadena; Seymour M. Linder; Yves J. Billoux, both of Baltimore, all of Md.

[73] Assignee: Alcolac Inc., Baltimore, Md.

[21] Appl. No.: 157,238

[22] Filed: Jun. 6, 1980

[51] Int. Cl.$^3$ .................. C07D 233/36; C07D 233/38
[52] U.S. Cl. ............................. 548/320; 260/348.59; 260/348.63; 544/316; 548/319; 524/548
[58] Field of Search ................. 548/319, 320; 544/316

[56] References Cited

U.S. PATENT DOCUMENTS

| | | | |
|---|---|---|---|
| 2,613,212 | 10/1952 | Hurwitz et al. | 548/318 |
| 2,694,695 | 11/1954 | Bortnick | 526/302 |
| 2,727,015 | 12/1955 | Auten et al. | 525/329 |
| 2,727,016 | 12/1955 | Hankins et al. | 526/263 |
| 2,828,224 | 3/1958 | Alps et al. | 428/473 |
| 2,831,833 | 4/1958 | Aycock et al. | 525/336 |
| 2,832,756 | 4/1958 | Melamed | 526/218 |
| 2,837,499 | 6/1958 | Melamed | 526/218 |
| 2,840,545 | 6/1958 | Yost | 526/263 |
| 2,871,223 | 1/1959 | Hankins et al. | 525/336 |
| 2,881,155 | 4/1959 | Hankins | 526/263 |
| 2,883,304 | 4/1959 | Kine et al. | 428/240 |
| 2,980,652 | 4/1961 | Melamed et al. | 526/262 |
| 3,014,042 | 12/1961 | Mantz | 548/320 |
| 3,350,363 | 10/1967 | Hurwitz | 526/263 |
| 3,356,627 | 12/1967 | Scott | 260/29.6 RB |
| 3,356,654 | 12/1967 | Sekmakas | 526/258 |
| 3,356,655 | 12/1967 | Sekmakas | 525/328 |
| 3,509,085 | 4/1970 | Sekmakas | 260/29.6 R |
| 3,852,291 | 12/1974 | Augstein et al. | 548/320 X |
| 4,104,220 | 8/1978 | Sims | 260/29.6 R |
| 4,111,877 | 9/1978 | Dixon et al. | 260/29.6 R |
| 4,151,142 | 4/1979 | Herman et al. | 260/29.6 R |

*Primary Examiner*—Richard A. Schwartz
*Attorney, Agent, or Firm*—Finnegan, Henderson, Farabow, Garrett & Dunner

[57] ABSTRACT

The invention provides new compounds which are cyclic alkylene ureas having hydroxyl and amine functionalities and which are produced by the reaction of an omega-amine alkyl alkylene urea, such as 2-aminoethyl ethylene urea, with an unsaturated glycidyl ether or ester, such as allyl glycidyl ether. The new compounds are monomers which may be incorporated in aqueous emulsion polymer systems and are useful as wet adhesion promoters for latex paints.

10 Claims, No Drawings

DERIVATIVES OF AMINOALKYL ALKYLENE UREAS

FIELD OF THE INVENTION

This invention relates to new chemical compounds, compositions, and their preparation and use. More particularly, this invention relates to the preparation of certain polymerizable alkylene ureas which are especially useful as monomers for latex paint compositions to promote wet adhesion of such paint compositions.

BACKGROUND OF THE INVENTION

The use of water-based emulsion polymer systems as protective and decorative coatings for many types of surfaces has become widespread. The so-called latex paint is commonly used by individuals in homes and industrially. While oil-based systems are known to retain their adhesive properties under wet or humid conditions, a characteristic called "wet adhesion," the tendency of many water-based coatings to lose their adhesive properties when wet has limited the usefulness of such coatings. This is particularly true for paints based on vinyl-acrylic or allacrylic latexes which otherwise are attractive as paint vehicles.

Paints intended for outdoor use are frequently exposed to moisture and humidity, as are paints used on interior surfaces in wet or humid atmospheres, such as in bathrooms and kitchens. Good wet adhesion is an important attribute of paints applied to those surfaces and others where resistance to water and abrasion is important, as where paints are exposed to washing or scrubbing, and where water-based paints are applied to glossy surfaces. In these situations, the need for improved wet adhesion of aqueous emulsion polymer systems is particularly great.

The art has recognized the problem of loss of adhesive properties in latex paints when wet, and a variety of additives to latex systems to improve wet adhesion has been proposed. For example, U.S. Pat. No. 3,356,655, issued on Dec. 5, 1967, and U.S. Pat. No. 3,509,085, issued on Apr. 28, 1970, disclose a number of ethylenically unsaturated hydroxy-functional amines which are said to be useful in improving adhesion and water resistance of latex paints. In addition, U.S. Pat. No. 4,111,877, issued on Sept. 5, 1978, discloses certain imidazolidinone derivatives which are said to improve the adhesive properties of latex paint.

It has now been found that latex-containing surface coatings and coating compositions having excellent wet adhesion properties can be produced by including in the monomer system one or a mixture of novel polymerizable cyclic alkylene ureas having amino, hydroxyl and allylic functionalities. In particular, the new compounds of this invention have been found to be especially useful in water-based latex-containing paints and can also be employed as comonomers in solution polymers.

SUMMARY OF THE INVENTION

In a broad sense, the invention relates to new polymerizable cyclic alkylene ureas having hydroxyl and amine functionalities and which are produced by the reaction of an omega-amino alkyl or substituted alkyl alkylene urea with an unsaturated glycidyl ether or ester. The compounds of the present invention have the generic formula:

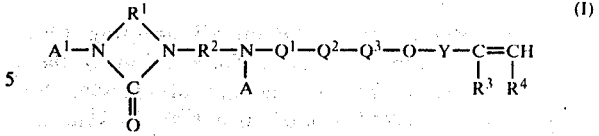

where $R^1$ is alkylene having 2 to 3 carbon atoms, and preferably $R^1$ is $C_2H_4$;

$R^2$ is alkylene having 2 to about 10, preferably 2 to 4, carbon atoms, and most preferably, $R^2$ is $C_2H_4$;

$R^3$ is H or $CH_3$, preferably H;

$R^4$ is H or $CH_3$ and may be the same as or different from $R^3$, and preferably $R^4$ is H;

$Q^1$ is $(R^5\text{-}O)_m$ where m is zero or an integer from 1 to about 100, preferably zero or 1 to about 75, and most preferably zero, and $R^5$ is a linear or branched alkylene, alkoxyalkylene, cycloalkylene, cycloalkoxyalkylene, arylalkylene or aryloxyalkylene residue having 2 to about 20, preferably 2 to 6, carbon atoms;

$Q^2$ is $\underset{\underset{CH_2OA^2}{|}}{CH-CH_2}$ or $\underset{\underset{OA^2}{|}}{CH_2-CH-CH_2}$, where $A^2$ is H or $(CH_2-\underset{\underset{CH_2-O-Q^3-Y-\underset{\underset{R^3}{|}}{CH}=\underset{\underset{R^4}{|}}{CH_2}}{|}}{CH}-O)_tH$ or $(CH-CH_2-O)_tH$
$\underset{CH_2-O-Q^3-Y-\underset{\underset{R_3}{|}}{CH}=\underset{\underset{R_4}{|}}{CH_2}}{|}$ where t is zero or an integer from 1 to 10, and preferably $Q^2$ is $\underset{\underset{CH_2OH}{|}}{CH-CH_2}$ or $\underset{\underset{OH}{|}}{CH_2-CH-CH_2}$;

$Q^3$ is $(O-R^6)_n$ where n is zero or an integer from 1 to about 100, preferably zero or from 1 to about 75, and most preferably n is zero, and may be the same as or different from m, and $R^6$ is a linear or branched alkylene, alkoxyalkylene, cycloalkylene, cycloalkoxyalkylene, arylalkylene or aryloxyalkylene residue having 2 to about 20, preferably 2 to 6, carbon atoms, and may be the same as or different from $R^5$;

Y is $CH_2$ or $-\underset{\underset{O}{||}}{C}-$, preferably $CH_2$;

A is H, $Q^4H$ or $-Q^4-Q^2-Q^5-O-Y-\underset{\underset{R^3}{|}}{C}=\underset{\underset{R^4}{|}}{CH}$ where $Q^4$ is $(R^7-O)_p$ where p is zero or an integer from 1 to about 100, preferably 1 to about 75, and may be the same as or different from m and n and preferably is the same as m, and $R^7$ is a linear or branched alkylene, alkoxyalkylene, cycloalkylene, cycloalkoxyalkylene, arylalkylene or aryloxyalkylene residue having 2 to about 20, preferably 2 to 6, carbon atoms, and may be the same as or different from $R^5$ and $R^6$ and preferably is the same as $R^5$;

$Q^5$ is $(O—R^8)_q$ where q is zero or an integer from 1 to about 100, preferably 1 to about 75, and may be the same as or different from m, n and p, and preferably is the same as n, and $R^8$ is a linear or branched alkylene, alkoxyalkylene, cycloalkylene, cycloalkoxyalkylene, arylalkylene or aryloxyalkylene residue having 2 to about 20, preferably 2 to 6, carbon atoms, and may be the same as or different from $R^5$, $R^6$ and $R^7$, and preferably is the same as $R^6$; and $Q^2$, Y, $R^3$ and $R^4$ are as defined above; and $A^1$ is H, $Q^6H$,

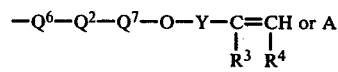

where $Q^6$ is $(R^9—O)_r$ where r is zero or an integer from 1 to about 100, preferably 1 to about 75, and may be the same as or different from m, n, p and q and preferably is the same as m, and $R^9$ is a linear or branched alkylene, alkoxyalkylene, cycloalkylene, cycloalkoxyalkylene, arylalkylene or aryloxyalkylene residue having 2 to about 20 preferably 2 to 6, carbon atoms, and may be the same as or different from $R^5$, $R^6$, $R^7$ and $R^8$, and preferably is the same as $R^5$;

$Q^7$ is $(O—R^{10})_s$ where s is zero or an integer from 1 to about 100, preferably 1 to about 75, and may be the same as or different from m, n, p, q and r, and preferably is the same as n, and $R^{10}$ is a linear or branched alkylene, alkoxyalkylene, cycloalkylene, cycloalkoxyalkylene, arylalkylene or aryloxyalkylene residue having 2 to about 20, preferably 2 to 6, carbon atoms, and may be the same as or different from $R^5$, $R^6$, $R^7$, $R^8$ and $R^9$, and preferably is the same as $R^6$; and $Q^2$, Y, $R^3$, $R^4$, and A are as defined above.

In the preferred embodiments of the compounds of the present invention, m and n are zero, whereby the compounds have the formula:

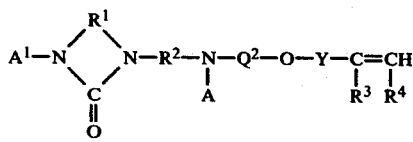

In the most preferred embodiments, $R^1$ is $C_2H_4$, $R^2$ is $C_2H_4$, A is either H or

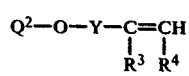

and $A^1$ is H whereby the compounds have the formula

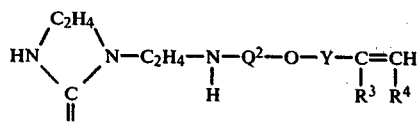

or the formula:

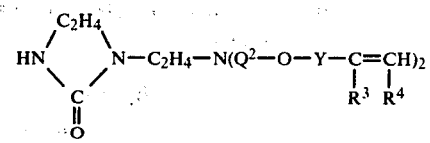

The compounds defined by formulae III and IV are aminoethyl imidazolidinones which contain hydroxyl functionality on the $Q^2$ moiety.

In keeping with the inventive concept, the invention also relates to the products of reacting an omega-amino alkyl or substituted alkyl alkylene urea with an unsaturated glycidyl ether or ester. Suitable omega-amino alkylene ureas have the formula:

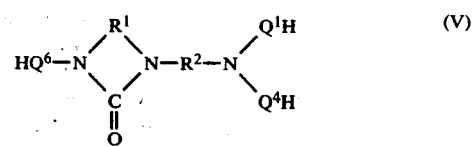

where $R^1$, $R^2$, $Q^1$, $Q^4$ and $Q^6$ are as defined above.

Preferably, the omega-amino alkylene ureas have the formula:

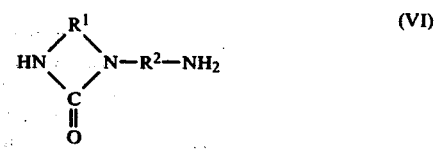

where $R^1$ and $R^2$ are as defined above. Most preferably both $R^1$ and $R^2$ are $C_2H_4$.

Suitable unsaturated glycidyl ethers and esters have the formula:

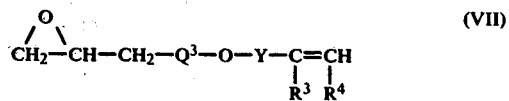

where $Q^3$, Y, $R^3$ and $R^4$ are as defined above. Preferably, unsaturated glycidyl ethers are used having the formula:

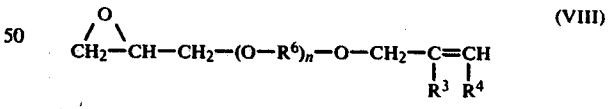

where $R^3$, $R^4$, $R^6$ and n are as defined above. It is preferred that $R^6$ is $C_2H_4$, and most preferably n is zero whereby the unsaturated glycidyl ether is:

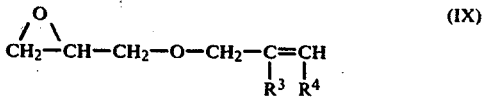

where $R^3$ and $R^4$ are as defined above.

In yet another aspect, the invention relates to making the compounds having the formula I above by the process which comprises reacting omega-amino alkyl or substituted alkyl alkylene ureas having the formula V (or VI) with unsaturated glycidyl ethers or esters having the formula VII. It is within the scope of the invention to use mixtures of the alkylene ureas and/or the glycidyl compound as reactants. The compounds of the present invention may properly be called adducts of omega-amino alkylene ureas and unsaturated glycidyl ethers or esters.

The compounds of this invention also are monomers capable of polymerization through their double bonds. Thus, the products of the reaction described above are useful as components of monomer systems, especially monomer systems used in forming aqueous emulsion polymers for coating surfaces. Accordingly, other aspects of the present invention include compositions comprising the monomers of the present invention, polymers made therefrom and compositions, especially acrylic and vinyl-acrylic latex paints comprising polymers made from the monomers of this invention. In addition, the present invention provides a method of enhancing the wet adhesion of aqueous polymer systems by incorporating the compounds of the present invention in the precursor monomer mixtures.

The general description of the invention above, along with the more detailed description of particular and preferred embodiments of the invention hereinafter, serve to illustrate the various aspects of this invention.

DETAILED DESCRIPTION OF PARTICULAR EMBODIMENTS

The monomers of the present invention may be derived from omega-amino alkylene ureas having the formula:

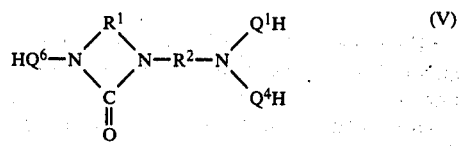

where $R^1$, $R^2$, $Q^1$, $Q^4$ and $Q^6$ are as defined above. The preferred omega-amino alkylene ureas are unsubstituted, having the formula:

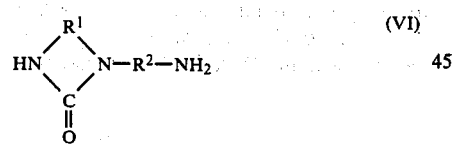

where $R^1$ is ethylene or propylene, preferably ethylene, and $R^2$ is an alkylene group having 2 to 10 carbon atoms, with 2 to 6 carbon atoms more preferred, and especially 2 to 4 carbon atoms.

Compounds of the formula VI may be made by first reacting a dialkylene triamine, $H_2N-R^1-NHR^2-NH_2$, with urea,

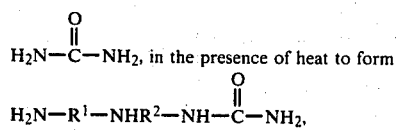

which when heated liberates ammonia and cyclizes to yield the omega-amino alkylene urea of formula VI and by-products which can be separated by distillation. The preferred omego-amino alkylene urea for use in the production of the monomers of this invention is 2-aminoethyl ethylene urea ("AEEU"), which is the compound having the formula VI where both $R^1$ and $R^2$ are ethylene:

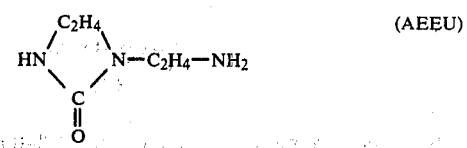

AEEU can be made by the reaction of diethylene triamine and urea as described above.

AEEU is a commercially available material. AEEU synthesis also is described in U.S. Pat. No. 2,613,212.

Substituted omega-amino alkylene ureas of formula V, including substituted derivatives of AEEU, may be formed by reacting an omega-amino alkylene urea of formula VI, such as AEEU, with one or more alkylene oxides having 2 to about 20, preferably 2 to about 6, most preferably 2 or 3, carbon atoms. For example, one mole of ethylene oxide,

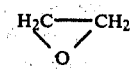

may be heated with one mole of AEEU to form:

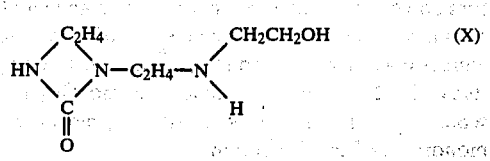

If a molar ratio of ethylene oxide to AEEU of 2:1 is used, the following substituted omega-amino alkylene urea is formed:

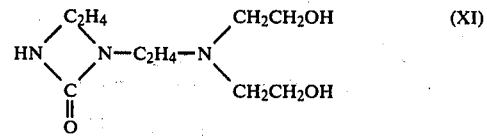

Subsequent moles of ethylene oxide would add to the ring nitrogen or to the hydroxyl moieties.

Similarly, if 1 mole and 2 moles, respectively, propylene oxide,

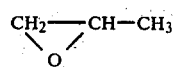

are reacted with AEEU, Structures XA and XIA would be two of the possible structures that would result:

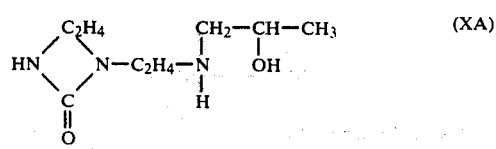

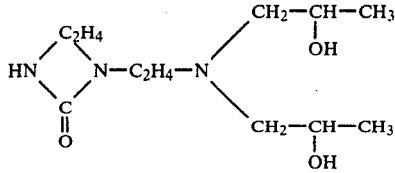
(XIA)

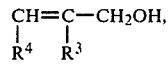

Included among contemplated alkoxylating agents are linear or branched alkylene oxides, such as ethylene oxide and propylene oxide, alkoxyalkylene oxides, such a butyl glycidyl ether, cycloalkylene oxides, such as cyclohexene oxide, and cycloalkoxyalkylene oxides, such as cyclohexyl glycidyl ether, aryl oxides such as styrene oxide, and aryloxyalkylene oxides such as phenyl glycidyl ether. Mixtures of alkylene oxides may be used. The preferred alkoxylating agents are ethylene oxide, propylene oxide and mixtures thereof.

In general, the number of moles of alkylene oxide can be selected as desired, with from 1 to about 100 being contemplated, preferably 1 to about 75, more preferably 1 to about 20, and most preferably 1 to about 10. The temperature conditions are selected to optimize the progress of the reaction considering the particular alkoxylating agent, and where more than 2 moles of alkylene oxide are used, it is generally desired to employ a catalyst, such as a Lewis acid or base. In general, process conditions, including temperatures and catalysts, as are known in the art in connection with alkoxylation of amines may be employed to produce substituted derivatives of AEEU or other omega-amino alkylene ureas which in turn can be used as starting reactants for the monomers of this invention.

In accordance with the process of the present invention, the omega-amino alkylene urea having the formula V (or VI), such as AEEU, or a mixture of omega-amino alkylene ureas, is reacted with an unsaturated glycidyl ether or ester having the formula:

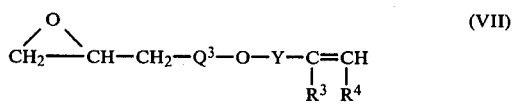
(VII)

where $Q^3$, Y, $R^3$ and $R^4$ are as defined above. It is preferred to use unsaturated glycidyl ethers having the formula:

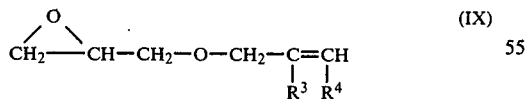
(IX)

where $R^3$ is H or $CH_3$, preferably H, and $R^4$ is H or $CH_3$, preferably H.

Compounds of the formula IX may be made by first reacting epichlorohydrin,

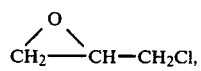

with an allylic alcohol,

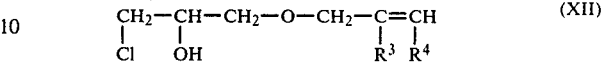

in the presence of a Lewis acid catalyst, such as $BF_3$ or $SnCl_4$, to produce the chlorohydrin:

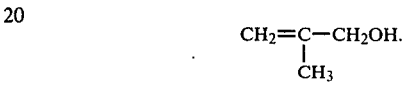
(XII)

The chlorohydrin XII may then be reacted with base, such as NaOH, to eliminate HCl and close the ring thereby forming an unsaturated glycidyl ether having the formula IX. Among suitable starting allylic alcohols are allyl alcohol, $CH_2$=CH—$CH_2OH$, crotyl alcohol, $CH_3$—CH=CH—$CH_2OH$, and methallyl alcohol $$CH_2=C-CH_2OH.$$
$$\phantom{CH_2=}|\phantom{-CH_2OH}$$
$$\phantom{CH_2=}CH_3$$

The most preferred unsaturated glycidyl ether for use in the production of the monomers of this invention is allyl glycidyl ether ("AGE"), which is the compound having the formula IX where both $R^3$ and $R^4$ are hydrogen:

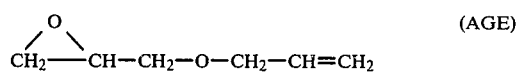
(AGE)

AGE can be made by the reaction of allyl alcohol and epichlorohydrin as described above, and is available commercially.

Substituted glycidyl ethers of formula VII where Y is $CH_2$, including substituted derivatives of AGE, may be formed by reacting the starting allylic alcohol, such as allyl alcohol, with one or more alkylene oxides having 2 to about 20, preferably 2 to about 6, most preferably 2 or 3, carbon atoms. For example, one mole of ethylene oxide may be reacted with one mole of allyl alcohol in the presence of an acid or base, such as sodium methoxide, to form an ethoxylated allyl alcohol:

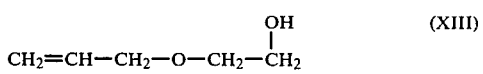
(XIII)

which then may be reacted with epichlorohydrin as described above. Subsequent moles of ethylene oxide would add to form a chain represented by the formula:

(XIV)

where n is the number of moles. In general, the number of moles n of alkylene oxide can be selected as desired, with from 1 to about 100 being contemplated, preferably 1 to about 75, more preferably 1 to about 20, and most preferably 1 to about 10. Allyl alcohol can also be propoxylated with propylene oxide to yield structures analagous to XIII and XIV. The processing conditions, such as temperature and catalyst, are selected to optimize the progress of the reaction considering the particular alkoxylating agent, and in general may be chosen as known in the art in connection with alkoxylation of alcohols.

Included among contemplated alkoxylating agents are linear or branched alkylene oxides, alkoxyalkylene oxides, cycloalkylene oxides, cycloalkoxyalkylene oxides, arylalkylene oxides, and aryloxyalkylene oxides as described above in connection with the alkoxylation of omega-amino alkylene ureas. Mixtures of alkylene oxides may be used. The preferred alkoxylating agents are ethylene oxide, propylene oxide and mixtures thereof.

It is within the purview of the invention to employ an unsaturated glycidyl ester having the formula:

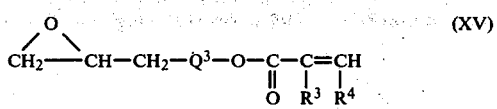
(XV)

where $Q^3$, $R^3$ and $R^4$ are as defined above. It is preferred to use a glycidyl ester having the formula:

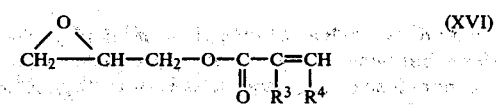
(XVI)

where $R^3$ is H or $CH_3$ and $R^4$ is H or $CH_3$, preferably H.

The most preferred unsaturated glycidyl esters are glycidyl methacrylate

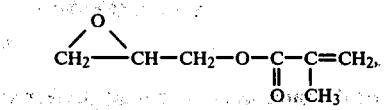

and glycidyl acrylate,

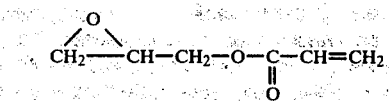

both of which are commercially available.

In accordance with the present invention, monomers useful as wet adhesion promoters in aqueous emulsion polymer systems are prepared by reacting an unsaturated glycidyl ether or ester having the formula:

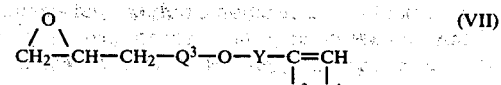
(VII)

with an omega-amino alkylene urea having the formula:

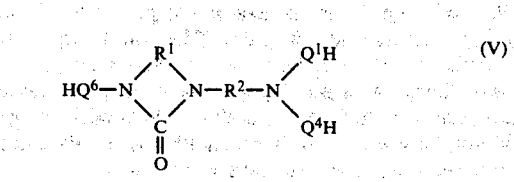
(V)

where $R^1$, $R^2$, $R^3$, $R^4$, $Q^1$, $Q^3$, $Q^4$ and Y are defined above.

The molar ratio of the glycidyl ether or ester to amino alkylene urea may vary. Ranges of molar ratio include from about 0.5 to about 10 moles of glycidyl ether or ester per mole of amino alkylene urea, preferably about 0.5 to about 8, more preferably about 0.5 to about 4, moles of glycidyl ether or ester per mole of amino alkylene urea. It is most preferred to use a molar ratio of glycidyl ether or ester to amino alkylene urea of about 1:1 to about 3:1.

The reaction may be effected over a wide temperature range. In general, a temperature and time period at least sufficient to effect the reaction are used. Effective temperatures may range from ambient temperature to about 500° C. Preferably, the temperature is from about 50° C. to about 250° C. The reaction time may be from about 1 to about 8 hours, preferably from about 2 to about 3 hours.

The most preferred embodiment of the process is the reaction of AGE with AEEU in a molar ratio of about 0.5 to about 10, preferably about 1 to about 4 and most preferably 1 to 2, moles of AGE per mole of AEEU at a temperature of from about 50° C. to about 250° C., preferably about 100° C. to about 200° C., and most preferably about 120° C.

In the process of the present invention, the oxirane ring of the glycidyl ether or ester reacts at one of the available amino nitrogen sites to form either

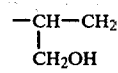

attached to the nigrogen or

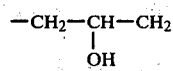

attached to the nitrogen. Therefore, the product of reaction will typically be a mixture of monomers having the formula:

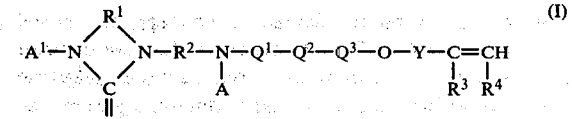
(I)

where $Q^2$ is the hydroxyl-containing moiety

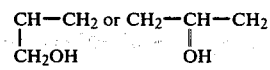

resulting from the opening of the oxirane ring on the glycidyl ether or ester; $R^1$ and $R^2$ are the alkyl groups on the amino alkylene urea as defined above; $Q^1$ is the substitution, if any, on the omega-amino nitrogen of amino alkylene urea as defined above; $Q^3$ is the substitution, if any, on the glycidyl ether or ester as defined above; Y is $CH_2$ if a glycidyl ether is used and

if a glycidyl ester is used; $R^3$ and $R^4$ are independently H or $CH_3$ as defined above in connection with the glycidyl ether or ester; and A and $A^1$ are as defined above and will depend upon which of the three available nitrogen sites are attacked.

It is possible to have the glycidyl ether or ester react further with the reaction product through the hydroxyl functionality on the $Q^2$ moiety, substituting the moiety $A^2$ as defined above in connection with formula I for the hydrogen. This further reaction may be accelerated by using an alkali metal alkoxide or aryloxide catalyst, such as sodium phenoxide, and a higher temperature.

In the chemically simplest, as well as most preferred, embodiment of the process of the invention wherein AGE is reacted with AEEU, the reaction product is believed to typically comprise a mixture of monomers having the formulas:

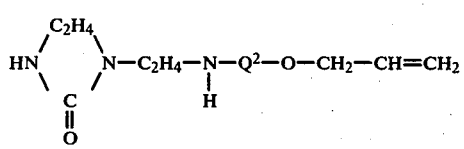
(XVII)

and

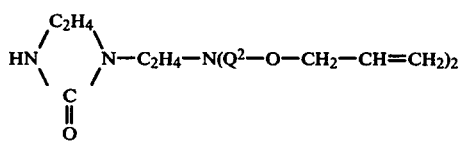
(XVIII)

where $Q^2$ is $CH_2-\underset{OH}{CH}-CH_2$ or $\underset{CH_2OH}{CH}-CH_2$.

In the case of formula XVIII, the two $Q^2$ moieties may be different from each other.

In general, the more glycidyl ether or ester that is used relative to the amount of omega-amino alkylene urea, the more diadduct, such as compound XVIII, that is formed.

In keeping with the inventive concept, the novel compounds produced by the reaction of an unsaturated glycidyl ether or ester with an omega-amino alkylene urea as described above are, individually, a part of the invention herein. Such compounds have the general formula:

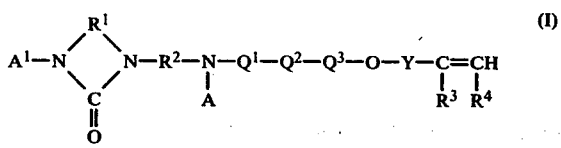
(I)

where $R^1$, $R^2$, $R^3$, $R^4$, $Q^1$, $Q^2$, $Q^3$, Y, A and $A^1$ are as defined above. Exemplary of compounds of the present invention are those having the formula I where $R^1$ is ethylene or propylene; $R^2$ is ethylene, propylene or butylene; $R^3$ is H or $CH_3$; $R^4$ is H or $CH_3$; $Q^1$ is $(C_2H_4O)_m$ or $(C_3H_5O)_m$ and m is zero or an integer from 1 to 20;

$Q^2$ is $\underset{CH_2OH}{CH}-CH_2$ or $CH_2-\underset{OH}{CH}-CH_2$; $Q^3$ is $(O-C_2H_4)_n$ or $(O-C_3H_5)_n$ and n is zero or an integer from 1 to 20; Y is $CH_2$ or

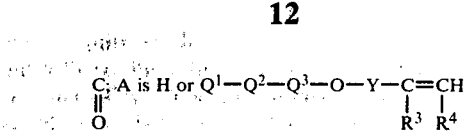

and $A^1$ is H or the same as A. It is contemplated that the $Q^1$, $Q^3$, $Q^4$, $Q^5$, $Q^6$ and $Q^7$ moieties can encompass mixtures of the residues defined above resulting from the use of mixtures of alkoxylating agents.

A preferred group of compounds of the present invention consists of compounds having the formula:

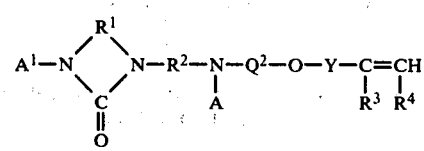
(II)

where $R^1$ is ethylene or propylene; $R^2$ is ethylene, propylene, butylene, pentylene, hexylene, heptylene, octylene, nonylene or decylene; $R^3$ is H or methyl; $R^4$ is H or methyl; $Q^2$ is $CH_2-\underset{OH}{CH}-CH_2$ or $\underset{CH_2OH}{CH}-CH_2$; Y is $CH_2$ or $\underset{O}{\overset{\|}{C}}$;

A is H or $Q^2-O-Y-\underset{R^3}{\overset{|}{C}}=\underset{R^4}{\overset{|}{CH}}$;

and $A^1$ is H or the same as A. The most preferred compounds are those having formulas XVII and XVIII above.

The reaction products and compounds of the present invention are polymerizable or copolymerizable through the unsaturation on the compounds. They may be used as comonomers in monomeric systems for forming aqueous emulsion polymers, including in compositions comprising such monomers as methyl acrylate, ethyl acrylate, methyl methacrylate, butyl acrylate, 2-ethyl hexyl acrylate, other acrylates, methacrylates and their blends, styrene, vinyl toluene, vinyl acetate, vinyl esters of higher carboxylic acids than acetic acid, acrylonitrile, acrylamide, vinyl chloride and the like, and mixtures thereof.

In particular, the reaction products and compounds of this invention may be incorporated in effective amounts in aqueous polymer systems to enhance the wet adhesion of paints made from the polymers. The commonly used monomers in making acrylic paints are butyl acrylate, methyl methacrylate, ethyl acrylate and mixtures thereof. In acrylic paint compositions at least 50% of the polymer formed is comprised of an ester of acrylic or methacrylic acid. The vinyl-acrylic paints usually include vinyl acetate and butyl acrylate or 2-ethyl hexyl acrylate. In vinyl-acrylic paint compositions, at least 50% of the polymer formed is comprised of vinyl acetate, with the remainder being selected from the esters of acrylic or methacrylic acid.

The novel reaction products and compounds of this invention may be added to the monomer composition from which acrylic or vinyl-acrylic polymers are formed in a concentration which may vary over a wide range. Preferably, the concentration is at least sufficient to improve the wet adhesion of paints made from the polymer composition. Concentrations may range from about 0.1% to about 20% by weight based on the total weight of monomers. It is preferred that the concentration be from about 0.2% to about 5%.

The monomer composition may be used in conjunction with other ingredients, such as various free radical sources to initiate polymerization, surfactants with or without colloids to protect particles from agglomeration, and buffers to maintain a desired pH during polymerization, all as known in the art of polymerization, and the polymerization may be carried out using conditions and techniques as are known in the art. In addition to making emulsion polymers, it is contemplated that the reaction products and compounds of the present invention be used to form solution copolymers.

The invention will now be illustrated by the following examples. The examples are not intended to be limiting of the scope of the present invention. In conjunction with the general and detailed descriptions above, the examples provide further understanding of the present invention. In the examples, percentages are by weight.

EXAMPLE 1

To 129 parts (1 mole) of 2-aminoethyl ethylene urea was added 114 parts (1 mole) of allyl glycidyl ether. The allyl glycidyl ether was added at such a rate as to allow the exothermic reaction to maintain a temperature of 80° C. The reaction product, characterized by NMR spectroscopy, gas and liquid chromatography and amine titrations is consistent with the product being a mixture of compounds having the structures of the formulas XVII and XVIII set forth above.

EXAMPLE 2

The reaction of Example 1 was repeated using 129 parts (1 mole) of 2-aminoethyl ethylene urea to which was added 228 parts (2 moles) of allyl glycidyl ether at such a rate as to maintain a temperature of 120° C. The reaction product characterized by NMR spectroscopy, gas and liquid chromatography, amine titrations and elemental analysis is consistent with the product being a mixture of compounds XVII and XVIII described above, with compound XVIII as the major component.

Elemental analysis: Calculated for $C_{17}H_{31}$, $N_3O_5$, C:57.12%; H:8.74%; N:11.76%; O:22.37%.

Found: C:56.84%; H:8.72%; N:11.85%; O:21.59%.

EXAMPLE 3

To 129 parts (1 mole) of 2-aminoethyl ethylene urea was added 57 parts (0.5 mole) of allyl glycidyl ether at such a rate as to maintain a reaction temperature of 120° C. The product, characterized by NMR spectroscopy, gas and liquid chromatography and amine titrations, is consistent with the product being a mixture of compound XVII, compound XVIII and unreacted 2-aminoethyl ethylene urea.

EXAMPLE 4

To 129 parts (1 mole) of 2-aminoethyl ethylene urea was added 193.8 parts (1.7 moles) of allyl glycidyl ether at such a rate as to maintain a reaction temperature of 120° C. The product, characterized by NMR spectroscopy, gas and liquid chromatography and amine titrations is consistent with the product being a mixture of compounds XVII and XVIII and unreacted 2-aminoethyl ethylene urea.

EXAMPLE 5

To 129 parts (1 mole) of 2-aminoethyl ethylene urea was added 456 parts (4 moles) of allyl glycidyl ether at such a rate as to maintain a reaction temperature of 120° C. The product, characterized by NMR spectroscopy, gas and liquid chromatography and amine titrations is consistent with the product being a mixture of compound XVII, compound XVIII and unreacted allyl glycidyl ether.

EXAMPLE 6

In this example, an adduct of 2-aminoethyl ethylene urea and glycidyl methacrylate was prepared. A mixture of 129 g. (1 mole) of 2-aminoethyl ethylene urea, 0.03 g. of methylene blue, and 0.6 g. of hydroquinone was heated to 60° C. To this mixture, 142 g (1 mole) of glycidyl methacrylate was added slowly over a period of 30 minutes, the temperature being maintained at 60° C. As confirmed by NMR analysis, the highly viscous product had the following structure:

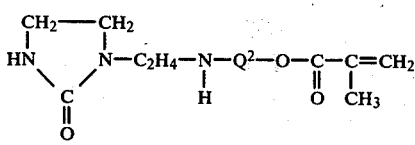

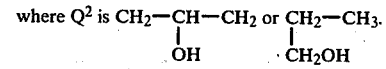

To illustrate the use of the monomers of this invention as wet adhesion promoters, and to compare them with other monomers, various emulsion polymer systems or latexes were prepared as described below. Then, semi-gloss paints were prepared from the emulsion polymers by first obtaining a pigment dispersion of:

| Materials | Weight in grams |
|---|---|
| Water | 460 |
| Magnesium aluminum silicate (Bentone LT) | 16 |
| Antifoamer (Nopco NXZ) (proprietary composition—non ionic yellow amber liquid) | 4 |
| Dispersant (Potassium Tripolyphosphate - 20%) | 20 |
| Dispersant (Tamol 850 - sodium salt of a polymeric carboxylic acid) | 20 |
| Wetting agent (Triton CF-10-alkylaryl polyether | 10 |
| Wet Edge Agent (Ethylene glycol) | 300 |
| Titanium dioxide (Titanox 2020) | 1100 |
| | 1930 |

These ingredients were mixed in high speed dispersing equipment until smooth. Then 160 g of the pigment dispersion was mixed with 179.5 g latex, 12.25 g ethylene glycol, 0.34 g antifoamer (Nopco NXZ), and 5.12 g Texanol (3-hydroxy isooctyl isobutyrate) using vigorous agitation.

The paints were evaluated for wet scrub properties using a modified ASTM-D 2486-69 Latex Paint Scrub Test. The test involved a 3 mil drawdown of high gloss, oil-based, enamel made on the full length of a Leneta Chart and air-dried seven days at room temperature. Next, simultaneous draw-downs of a control paint and the paint being evaluated across the gloss enamel near the center of the chart were made before air-drying for two days at room temperature. The Leneta Chart was fastened to the glass base plate and mounted in the Gardner scrub tester. The scrub brush was soaked in a 2 percent solution of Triton X-100 (octyl phenoxy polyethoxy ethanol) for 30 minutes, then shaken vigorously to remove excess detergent solution. Ten grams of a scrub medium (well mixed 497 g water, 10 g cellosize WP-4400 hydroxy ethyl cellulose, 20 g Triton X-100, 20 g. Trisodium Phosphate, 450 g #22 Silica and 2 g Acetic Acid) were spread evenly over the brush bristles. The brush was mounted in the holder of the Gardner scrub tester and the panel was wetted with 5 g water before beginning test. After each 250 cycles, before failure, 10 g scrub media was added, the brush was remounted and 5 g additional water was placed on the chart in the path of the brush before continuing the test.

In the following Examples 7-13, the reaction product obtained in Example 1 was used in acrylic latex emulsions. The acrylic latex emulsions used were systems in which at least 50 percent of the polymer formed is comprised of an ester of acrylic or methacrylic acid. The emulsions were used in the semi-gloss paint formulation described above and evaluated for wet scrub properties.

EXAMPLE 7

An acrylic emulsion polymer, for paint application, containing 3 percent of the product obtained in Example 1 was prepared using the following procedure:

| Materials | Weight in grams |
| --- | --- |
| Butyl acrylate | 255 |
| Methyl Methacrylate | 230 |
| Product of Example 1 | 15 |
| Blend of sodium fatty alcohol polyether sulfate and octyl phenoxypoly(oxyethylene) ethanol surfactant at 42% solids | 39.7 |
| Sodium persulfate | 1.8 |
| Sodium metabisulfite | 1.5 |
| Water, deionized | 450 |
| | 993 |

Solutions of 1.8 g sodium persulfate in 36 g water and of 1.5 g sodium metabisulfite in 60 g water were prepared. There was then prepared a pre-emulsion of 150 g water, surfactant blend, butyl acrylate, and methyl methacrylate. A one liter resin reactor was charged with 204 g water and product of Example 1. The reactor was purged with nitrogen and heated to 60° C. After the reactor reached 60° C., there was added 18 ml of the persulfate and 8 ml of metabisulfite solution, followed by addition of one percent of the pre-emulsion. After allowing seed latex formation for about 10 minutes, the pre-emulsion was added over a 2-2.5 hour period and the persulfate-metabisulfite solutions over 2.5 to 3 hours while holding the reactor temperature between 60°-65° C. The total polymerization time was approximately 3.5 hours. The latex was cooled and filtered. The latex was adjusted to 46% solids and a pH of 9.5 with ammonium hydroxide.

The emulsion polymer was used in the semi-gloss paint formulation that included titanium dioxide pigment. When the paint was subjected to the wet scrub test described above, no failure occurred by 1500 cycles indicating that the paint has excellent wet scrub properties.

EXAMPLE 8

An emulsion polymer was prepared in a manner similar to that in Example 7 with a monomer system containing 6.0 percent product of Example 1, 51 percent butyl acrylate and 43 percent methyl methacrylate. The emulsion polymer was used in the semi-gloss paint formulation. No failure occurred in the wet scrub test by 1500 cycles indicating that the paint has excellent wet scrub properties.

EXAMPLE 9

An emulsion polymer was prepared in a manner similar to that in Example 7 with a monomer system containing 2.0 percent product of Example 1, 66 percent ethyl acrylate and 32 percent methyl methacrylate. The emulsion polymer was used in the semi-gloss paint formulation. No failure occurred in the wet scrub test by 1500 cycles indicating that the paint has excellent wet scrub properties.

EXAMPLE 10

An emulsion polymer was prepared in a manner similar to that in Example 7 with a monomer system containing 2.0 percent product of Example 1, 68 percent ethyl acrylate, and 30 percent styrene. The emulsion polymer was used in the semi-gloss paint formulation. No failure occurred in the wet scrub test by 1500 cycles indicating that the paint has excellent wet scrub properties.

EXAMPLE 11

An emulsion polymer was prepared in a manner similar to that in Example 7 with a monomer system containing 1.5 percent of product of Example 1, 51 percent butyl acrylate and 47.5 percent methyl methacrylate. The emulsion polymer was used in the semi-gloss paint formulation. No failure occurred in the wet scrub test by 1500 cycles indicating that the paint has excellent wet scrub properties.

EXAMPLE 12

An emulsion polymer was prepared in a manner similar to that in Example 7 with a monomer system containing 0.75 percent product of Example 1, 51 percent butyl acrylate and 48.25 percent methyl methacrylate. The emulsion polymer was used in the semi-gloss paint formulation. No failure occurred in the wet scrub test by 1500 cycles indicating that the paint has excellent wet scrub properties.

EXAMPLE 13

An emulsion polymer was prepared in a manner similar to that in Example 7 with a monomer system containing 0.3 percent of product of Example 1, 51 percent butyl acrylate and 48.7 percent methyl methacrylate. The emulsion polymer was used in the semi-gloss paint formulation. No failure occurred in the wet scrub test by 1500 cycles indicating that the paint has excellent wet scrub properties.

EXAMPLE 14

An emulsion polymer was prepared in a manner similar to that in Example 7, but rather than using with a monomer system containing a product of the present invention, a monomer system containing 2 percent methacrylic acid, 51 percent butyl acrylate and 47 percent methyl methacrylate was used. The emulsion polymer was used in the semi-gloss paint formulation. Failure occurred by 47 cycles indicating that this paint has poor wet scrub properties.

In the following Examples 15-18 the reaction product obtained in Example 1 was used in vinyl acrylic emulsions. The vinyl acrylic emulsions used were polymerizing systems in which at least 50 percent of the monomer composition is vinyl acetate, the remainder being selected from the esters of acrylic or methacrylic acid. Again, the emulsions were tested for wet scrub properties using the test set forth above.

EXAMPLE 15

A vinyl acrylic emulsion polymer, for paint application, containing 1.5 percent of the product obtained in Example 1 was prepared using the following procedure:

| Materials | Weight in grams |
| --- | --- |
| Vinyl acetate | 428.2 |
| Butyl acrylate | 119.5 |
| Product of Example 1 | 8.3 |
| Blend of sodium fatty alcohol poly(oxyethylene) sulfate and octyl phenoxypoly(oxyethylene) ethanol surfactant at 46 percent solids | 58.9 |
| Sodium carbonate | 1.5 |
| Hydroxyethyl ether of cellulose (Natrosol 180 LR) | 0.56 |
| Ammonium persulfate | 3.89 |
| Sodium metabisulfite | 3.33 |
| Water, deionized | 375.4 |
| | 999.58 |

A one liter reactor was charged with 264.2 g water, 5.8 g surfactant, and the hydroxyethyl cellulose. The reactor was purged with nitrogen and heated to 70° C. A solution of sodium metabisulfite, 53 g surfactant and 55.6 g water was prepared. After 8 ml of solution was removed, for initiation, the product of Example 1 was mixed into the solution. A solution of ammonium persulfate, sodium carbonate and 55.6 g water was prepared. The vinyl acetate and butyl acrylate were blended together. The 8 ml of metabisulfite solution, without the product of Example 1, was added to the reactor at 70° C. together with 5.5 ml of the ammonium persulfate solution and the monomer blend was then added dropwise. The monomer blend was added over a period of 4 hours. The metabisulfite solution was added over 4 hours and the persulfate solution over 4.5 hours. The total polymerization time was 5 hours for the run. The latex product was cooled and then filtered. The solids were adjusted to 46% and the pH raised to 9.5 with ammonium hydroxide.

The emulsion polymer was used in the semi-gloss paint formulation described above. No failure occurred in the wet scrub test by 1500 cycles indicating that the paint has excellent wet scrub properties.

EXAMPLE 16

An emulsion polymer was prepared in a manner similar to that in Example 15 with a monomer system containing 1.5 percent product of Example 1, 15.0 percent 2-ethyl hexyl acrylate and 83.5 percent vinyl acetate. The emulsion polymer was used in the semi-gloss paint formulation. No failure occurred in the wet scrub test by 1500 cycles indicating that the paint has excellent wet scrub properties.

EXAMPLE 17

An emulsion polymer was prepared in a manner similar to that in Example 15 with a monomer system containing 2.2 percent product of Example 1, 20.8 percent butyl acrylate and 77 percent vinyl acetate. The emulsion polymer was used in the semi-gloss paint formulation. No failure occurred in the wet scrub test by 1500 cycles indicating that the paint has excellent wet scrub properties.

EXAMPLE 18

An emulsion polymer was prepared in a manner similar to that in Example 15 with a monomer system containing 1.0 percent product of Example 1, 22.0 percent butyl acrylate and 77 percent vinyl acetate. The emulsion polymer was used in the semi-gloss paint formulation. No failure occurred in the wet scrub test by 1500 cycles indicating that the paint has excellent wet scrub properties.

In the following Examples 19-22 products prepared by reacting other than equimolar quantities of 2-aminoethyl ethylene urea with allyl glycidyl ether were used in forming the emulsion polymer.

EXAMPLE 19

An emulsion polymer was prepared in a manner similar to that in Example 7 with a monomer system containing 1.0 percent product of Example 2, 51 percent butyl acrylate and 48.0 percent methyl methacrylate. The emulsion polymer was used in the semi-gloss paint formulation. No failure occurred in the wet scrub test by 1500 cycles indicating that the paint has excellent wet scrub properties.

EXAMPLE 20

An emulsion polymer was prepared in a manner similar to that in Example 15 with a monomer system containing 1.0 percent product of Example 2, 22.0 percent butyl acrylate and 77 percent vinyl acetate. The emulsion polymer was used in the semi-gloss paint formulation. No failure occurred in the wet scrub test by 1500 cycles indicating that the paint has excellent wet scrub properties.

EXAMPLE 21

An emulsion polymer was prepared in a manner similar to that in Example 15 with a monomer system containing 1.0 percent product of Example 5, 22.0 percent butyl acrylate and 77 percent vinyl acetate. The emulsion polymer was used in the semi-gloss paint formulation. No failure occurred in the wet scrub test by 1500 cycles indicating that the paint has excellent wet scrub properties.

EXAMPLE 22

An emulsion polymer was prepared in a manner similar to that in Example 15 with a monomer system containing 1.0 percent product of Example 3, 22.0 percent butyl acrylate and 77 percent vinyl acetate. The emulsion polymer was used in the semi-gloss paint formulation. No failure occurred in the wet scrub test by 1500 cycles indicating that the paint has excellent wet scrub properties.

EXAMPLE 23

An acrylic emulsion polymer, for paint application, containing 1 percent of the glycidyl methacrylate-AEEU product obtained in Example 6 was prepared using the following procedure:

| Materials | Weight in grams |
| --- | --- |
| Butyl acrylate | 255 |
| Methyl methacrylate | 240 |
| Product of Example 6 | 5 |

| Materials | Weight in grams |
|---|---|
| Blend of Sodium fatty alcohol polyether sulfate and octyl phenoxypoly(oxyethylene) ethanol surfactant at 42% solids | 39.7 |
| Sodium persulfate | 1.8 |
| Sodium metabisulfite | 1.5 |
| Water, deionized | 450.0 |
| | 993 |

Solutions of 1.8 g sodium persulfate in 36 g water and 1.5 g sodium meta-bisulfite in 60 g water were prepared. There was then prepared a pre-emulsion of 150 g water, surfactant blend, butyl acrylate, product of Example 6, and methyl methacrylate. A one liter resin reactor was charged with 204 g water. The reactor was purged with nitrogen and heated to 60° C. After the reactor reached 60° C., there was added 18 ml of the persulfate and 8 ml of metabisulfite solution followed by addition of one percent of the pre-emulsion. After allowing seed latex formation for about 10 minutes, the pre-emulsion was added over a 2–2.5 hour period and the persulfate-metabisulfite solutions over 2.5–3 hours while holding the reactor temperature between 60°–65° C. The total polymerization time was approximately 3.5 hours. The latex was cooled and filtered. The latex was adjusted to 46% solids and a pH of 9.5 with ammonium hydroxide.

The emulsion polymer was used in the semi-gloss paint formulation that included titanium dioxide pigment. When the paint was subjected to the wet scrub test described above, no failure occurred by 1500 cycles indicating that the paint has excellent wet scrub properties.

EXAMPLE 24

An emulsion polymer was prepared in a manner similar to that in Example 23 with a monomer system containing 0.75 percent product of Example 6, 51 percent butyl acrylate and 48.25 percent methyl methacrylate. The emulsion polymer was used in the semi-gloss paint formulation. No failure occurred in the wet scrub test by 1500 cycles indicating that the paint has excellent wet scrub properties.

In the following Examples 25–37, monomers other than those of the present invention were incorporated into acrylic or vinyl acrylic emulsion polymer systems and tested. These examples demonstrate the unpredictability of wet adhesion functionality in general and the excellent wet adhesion promotion properties of the compounds of the present invention.

EXAMPLE 25

An emulsion polymer was prepared in a manner similar to that in Example 15 with a monomer system containing 2 percent maleic anhydride-AEEU reaction product, 21 percent butyl acrylate and 77 percent vinyl acetate. The emulsion polymer was used in the semi-gloss paint formulation. Failure in the wet scrub test occurred by 68 cycles indicating that the paint has poor wet scrub properties.

EXAMPLE 26

An emulsion polymer was prepared in a manner similar to that in Example 15 with a monomer system containing 1.5 percent allyl N-ethyl-β-(1-ethylene ureido) carbamate (disclosed in U.S. Pat. No. 4,111,877), 21.5 percent butyl acrylate and 77 percent vinyl acetate. The emulsion polymer was used in the semi-gloss paint formulation. Failure in the wet scrub test occurred by 730 cycles indicating that the paint has fair wet scrub properties.

EXAMPLE 27

An emulsion polymer was prepared in a manner similar to that in Example 7 with a monomer system containing 0.75 percent AGE-hydroxyethyl ethylene urea product (disclosed in U.S. Pat. No. 3,509,085), 51 percent butyl acrylate, and 48.25 percent methyl methacrylate. The emulsion polymer was used in the semi-gloss paint formulation. Failure in the wet scrub test occurred by 530 cycles indicating that the paint has fairly poor wet scrub properties.

EXAMPLE 28

An emulsion polymer was prepared in a manner similar to that in Example 15 with a monomer system containing 1.5 percent AGE-hydroxyethyl ethylene urea product (disclosed in U.S. Pat. No. 3,509,085), 21.5 percent butyl acrylate and 77 percent vinyl acetate. The emulsion polymer was used in the semi-gloss paint formulation. Failure occurred in the wet scrub test by 241 cycles indicating that the paint has poor wet scrub properties.

EXAMPLE 29

An emulsion polymer was prepared in a manner similar to that in Example 23 with a monomer containing 3 percent of Dimethylaminoethyl Methacrylate (Commercially available), 48.5 percent butyl acrylate and 48.5 percent methyl methacrylate. The emulsion polymer was used in the semi-gloss paint formulation. Failure occurred in the wet scrub test by 943 cycles indicating that the paint has fairly good wet scrub properties.

EXAMPLE 30

An emulsion polymer was prepared in a manner similar to that in Example 15 with a monomer system containing 1 percent of product of Example 4, 22 percent butyl acrylate and 77 percent vinyl acetate. The emulsion polymer was used in the semi-gloss paint formulation. No failure occurred in the wet scrub test by 1500 cycles indicating that the paint has excellent wet scrub properties.

EXAMPLE 31

An emulsion polymer was prepared in a manner similar to that in Example 7 with a monomer system containing 3 percent of an AGE-dimethyl urea adduct, 51 percent butyl acrylate and 46 percent methyl methacrylate. The emulsion polymer was used in the semi-gloss paint formulation. Failure occurred in the wet scrub test by 259 cycles indicating that the paint has poor wet scrub properties.

EXAMPLE 32

An emulsion polymer was prepared in a manner similar to that in Example 15 with monomer system containing 3 percent Dimethylaminoethyl Methacrylate (Commercially available), 20 percent butyl acrylate and 77 percent vinyl acetate. The emulsion polymer was used in the semi-gloss paint formulation. Failure occurred in the wet scrub test by 1076 cycles indicating that the paint has fairly good wet scrub properties.

EXAMPLE 33

An emulsion polymer was prepared in a manner similar to that in Example 7 with a monomer system containing 1.5 percent of AGE-dimethyl hydantoin adduct, 51 percent butyl acrylate and 47.5 percent methyl methacrylate. The emulsion polymer was used in the semi-gloss paint formulation. Failure occurred in the wet scrub test by 62 cycles indicating that the paint has poor wet scrub properties.

EXAMPLE 34

An emulsion polymer was prepared in a manner similar to that in Example 7 with a monomer system containing 1.5 percent of ethylene urea, 51 percent butyl acrylate and 47.5 percent methyl methacrylate. The emulsion polymer was used in the semi-gloss paint formulation. Failure occurred in the wet scrub test by 50 cycles indicating that the paint has poor wet scrub properties.

EXAMPLE 35

An emulsion polymer was prepared in a manner similar to that in Example 7 with a monomer system containing 1.5 percent of an AGE-triethanolamine adduct, 51 percent butyl acrylate and 47.5 percent methyl methacrylate. The emulsion polymer as used in the semi-gloss paint formulation. Failure occurred in the wet scrub test by 191 cycles indicating that the paint has poor wet scrub properties.

EXAMPLE 36

An emulsion polymer was prepared in a manner similar to that in Example 15 with a monomer system containing 1.5 percent of an AGE-N,N-dimethyl ethylene diamine adduct, 21.5 percent butyl acrylate and 77 percent vinyl acetate. The emulsion polymer was used in the semi-gloss paint formulation. Failure occurred in the wet scrub test by 81 cycles indicating that the paint has poor wet scrub properties.

EXAMPLE 37

An emulsion polymer was prepared in a manner similar to that in Example 7 with a monomer system containing 1.5 percent allyl acetoacetate, 51 percent butyl acrylate and 47.5 percent methyl methacrylate. The emulsion polymer was used in the semi-gloss paint formulation. Failure occurred in the wet scrub test by 136 cycles indicating that the paint has poor wet scrub properties.

EXAMPLE 38

For comparison, a paint was made using an acrylic emulsion prepared in a manner similar to that in Example 7 but containing no wet adhesion promoter. The paint was subjected to the web scrub test and failure occurred by 94 cycles.

EXAMPLE 39

One of the best available commercial acrylic resin emulsion paints, known as A-100 Gloss Latex Paint (House & Trim) Perma White 100-9042 A8W24 and made by Sherwin-Williams Company, Cleveland, Ohio 44101, was subjected to the wet scrub test. Failure occurred by 507 cycles. The complete chemical composition of this paint is not known.

The results of the experiments reported in the Examples have been complied in the following tables:

TABLE I

Wet Scrub Test Results for Paints

| Example No. Acrylic Polymer | Wet Adhesion Promoter | Percent Level | Cycles to Failure |
|---|---|---|---|
| 8 | Product of Example 1 | 6.0 | No Failure |
| 7 | Product of Example 1 | 3.0 | No Failure |
| 9 | Product of Example 1 | 2.0 | No Failure |
| 10 | Product of Example 1 | 2.0 | No Failure |
| 11 | Product of Example 1 | 1.6 | No Failure |
| 12 | Product of Example 1 | 0.75 | No Failure |
| 13 | Product of Example 1 | 0.3 | No Failure |
| 14 | Methacrylic Acid | 2.0 | 47 |
| 38 | None | 0 | 94 |
| 39 | Unknown | Unknown | 507 |
| Vinyl-acrylic Polymer | | | |
| 15 | Product of Example 1 | 1.5 | No Failure |
| 16 | Product of Example 1 | 1.5 | No Failure |
| 17 | Product of Example 1 | 2.2 | No Failure |
| 18 | Product of Example 1 | 1.0 | No Failure |

*In those cases where no failure occurred by 1500 cycles, the test was discontinued.

The wet scrub results in Table I clearly shows that the Product of Example 1 in paint latexes promotes wet scrub properties. The Product of Example 1 is effective at levels of from about 0.1 to about 9 percent, but the preferable level is from about 0.2 to about 5 percent by weight.

TABLE II

Wet Scrub Test Results for Paints

| Example No. Acrylic Polymer | Wet Adhesion Promoter | Percent Level | Cycles to Failure* |
|---|---|---|---|
| 19 | Product of Example 2 | 1.0 | No Failure |
| 23 | Product of Example 6 | 1.0 | No Failure |
| 24 | Product of Example 6 | 0.75 | No Failure |
| Vinyl-acrylic Polymer | | | |
| 18 | Product of Example 1 | 1.0 | No Failure |
| 20 | Product of Example 2 | 1.0 | No Failure |
| 21 | Product of Example 5 | 1.0 | No Failure |
| 22 | Product of Example 3 | 1.0 | No Failure |

*In those cases where no failure occurred by 1500 cycles, the test was discontinued.

The wet scrub results in Table II show that the Products of Examples 1, 2, 3, 5 and 6 are effective wet adhesion promoting monomers. It is more difficult to obtain good wet scrub results with vinyl acetate-acrylic emulsion polymer paints than with acrylic paint. This is especially true of the product of Example 6 which at some percent levels did not show good wet adhesion.

TABLE III

Wet Scrub Test Results for Paints

| Example No. Acrylic Polymer | Wet Adhesion Promoter | Percent Level | Cycles to Failure* |
|---|---|---|---|
| 12 | Product of Example 1 | 0.75 | No Failure |
| 25 | Allyl glycidyl ether-hydroxy ethyl ethylene urea reaction product | 0.75 | 530 |
| Vinyl-acrylic Polymer | | | |
| 15 | Product of Example 1 | 1.5 | No Failure |
| 25 | Maleic Anhydride-Amino-ethyl ethylene urea reaction product | 2.0 | 68 |
| 26 | Allyl N-ethyl-B-(1-ethylene ureido) carbamate | 1.5 | 730 |

TABLE III-continued

Wet Scrub Test Results for Paints

| Example No. Acrylic Polymer | Wet Adhesion Promoter | Percent Level | Cycles to Failure* |
|---|---|---|---|
| 28 | Allyl glycidyl ether-Hydroxy ethyl ethylene urea reaction product | 1.5 | 241 |

*In those cases where no failure occurred by 1500 cycles, the test was discontinued.

The results in Table III show that the Product of Example 1 is superior to many other monomers that may be used as wet adhesion promoters. The allyl N-ethyl-B(1-ethylene ureido) carbamate (U.S. Pat. No. 4,111,877-Dixon) and the allyl glycidyl ether-Hydroxy ethyl ethylene urea reaction product (U.S. Pat. No. 3,509,085-Sekmakas) monomers are good wet adhesion promoters but not as good as the Product of Example 1.

TABLE IV

Wet Scrub Test Results for Paints

| Example No. Acrylic Polymer | Wet Adhesion Promoters | Percent Level | Cycles to Failure* |
|---|---|---|---|
| 7 | Product of Example 1 | 3.0 | No Failure |
| 29 | Dimethylaminoethyl Methacrylate | 3.0 | 943 |
| 34 | Ethylene urea | 1.5 | 50 |
| 31 | Allyl glycidyl ether-Dimethyl urea reaction product | 3.0 | 259 |
| 33 | Allyl glycidyl ether-Dimethyl Hydantoin reaction product | 1.5 | 62 |
| 35 | Allyl glycidyl ether-Triethanolamine reaction product | 1.5 | 191 |
| 37 | Allyl Acetoacetate | 1.5 | 136 |
| Vinyl-Acrylic Polymer | | | |
| 30 | Product of Example 4 | 1.0 | No Failure |
| 36 | Allyl glycidyl ether-N,N-Dimethyl ethylene diamine reaction product | 1.5 | 81 |
| 32 | Dimethylaminoethyl Methacrylate | 3.0 | 1076 |

*In those cases where no failure occurred by 1500 cycles, the test was discontinued.

The results of evaluations in Table IV indicate the wide variation in wet adhesion promoting potential or different monomers.

The scope of the present invention is not limited by the description and examples herein, and modifications can be made without departing from the spirit of the invention. For example, the reaction products and compounds of this invention may be used in coating compositions other than latex paints, such as paper coatings, printing inks, textile sizing agents, binders and the like. Moreover, modifications could be made in the structures without affecting the functioning of the amine and hydroxyl groups of the compounds of this invention.

What is claimed is:

1. A compound having the formula:

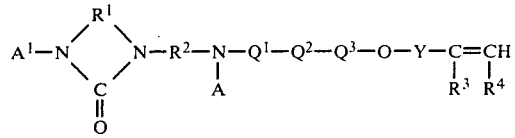

where
$R^1$ is alkylene having 2 to 3 carbon atoms;
$R^2$ is alkylene having 2 to about 10 carbon atoms;
$R^3$ is H or $CH_3$;
$R^4$ is H or $CH_3$ and may be the same as or different from $R^3$;
$Q^1$ is $(R^5-O)_m$ where m is zero or an integer from 1 to about 100, and $R^5$ is a linear or branched alkylene, alkoxyalkylene, cycloalkylene, cycloalkoxyalkylene, arylalkylene, or aryloxyalkylene residue having 2 to about 20 carbon atoms;

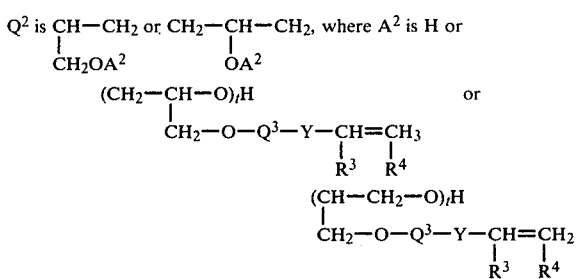

where t is zero or an integer from 1 to 10;
$Q^3$ is $(O-R^6)_n$ where n is zero or an integer from 1 to about 100 and may be the same as or different from m, and $R^6$ is a linear or branched alkylene, alkoxyalkylene, cycloalkylene, cycloalkoxyalkylene, arylalkylene or aryloxyalkylene residue having 2 to about 20 carbon atoms, and may be the same as or different from $R^5$;

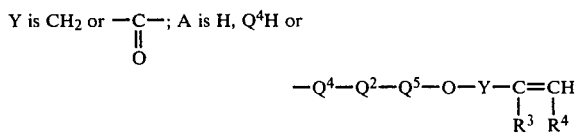

where
$Q^4$ is $(R^7-O)_p$ where p is zero or an integer from 1 to about 100 and may be the same as or different from m and n, and $R^7$ is a linear or branched alkylene, alkoxyalkylene, cycloalkylene, cycloalkoxyalkylene, arylalkylene, or aryloxyalkylene residue having 2 to about 20 carbon atoms, and may be the same as or different from $R^5$ or $R^6$;
$Q^5$ is $(O-R^8)_q$ where q is zero or an integer from 1 to about 100 and may be the same as or different from m, n and p, and $R^8$ is a linear or branched alkylene, alkoxyalkylene, cycloalkylene, cycloalkoxyalkylene, arylalkylene, or aryloxyalkylene residue having 2 to about 20 carbon atoms, and may be the same as or different from $R^5$, $R^6$ and $R^7$; and

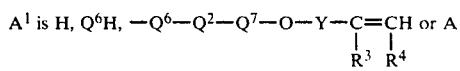

where $Q^6$ is $(R^9-O)_r$ where r is zero or an integer from 1 to about 100 and may be the same as or different from m, n, p and q, and $R^9$ is a linear or branched alkylene, alkoxyalkylene, cycloalkylene, cycloalkoxyalkylene, arylalkylene, or aryloxyalkylene residue having 2 to about 20 carbon atoms, and may be the same as or different from $R^5$, $R^6$, $R^7$ and $R^8$; and $Q^7$ is $(O-R^{10})_s$ where s is zero or an integer from 1 to about 100 and may be the same as or different from m, n, p, q and r, and $R^{10}$ is a linear or branched alkylene, alkoxyalkylene, cycloalkylene, cycloalkoxyalkylene, arylalkylene or aryloxyalkylene residue having 2 to about 20 carbon atoms, and may be the same as or different from $R^5$, $R^6$, $R^7$, $R^8$, and $R^9$.

2. A compound according to claim 1 wherein $R^2$ is ethylene, propylene or butylene; $Q^1$ is $(C_2H_4-O)_m$ or $(C_3H_5-O)_m$ and m is zero or an integer from 1 to 100; $Q^3$ is $(O-C_2H_4)_n$ and n is zero or an integer from 1 to 100; A is H or

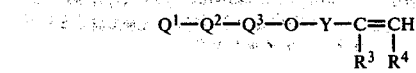

and $A^1$ is H or the same as A.

3. A compound according to claim 1 having the formula:

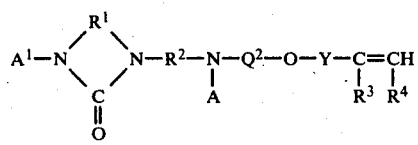

where $R^1$, $R^2$, $R^3$, $R^4$ and Y are as defined in claim 1; $Q^2$ is

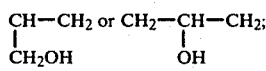

A is H or

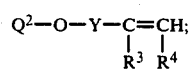

and $A^1$ is H or the same as A.

4. A compound according to claim 3 wherein Y is $CH_2$.

5. A compound according to claim 3 wherein Y is

6. A compound selected from the group consisting of:

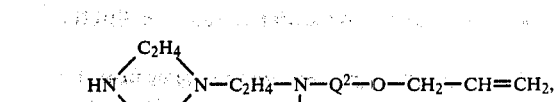

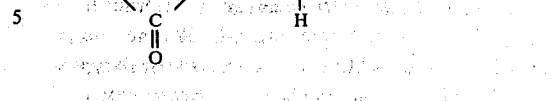

and

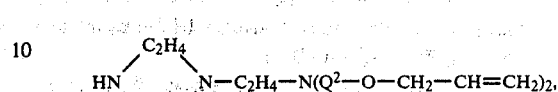

where $Q^2$ is $$CH_2-CH-CH_2 \text{ or } CH-CH_2$$
$$\qquad\quad | \qquad\qquad\quad |$$
$$\qquad\quad OH \qquad\qquad CH_2OH$$

and $A^1$ is $Q^2-O-CH_2-CH=CH_2$.

7. A composition of matter made by reacting (1) an unsaturated glycidyl ether or ester having the formula:

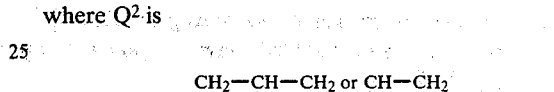

where $R^3$ is H or $CH_3$;

$R^4$ is H or $CH_3$ and may be the same as or different from $R^3$;

Y is $CH_2$ or 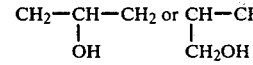; and $Q^3$ is $(O-R^6)_n$ where n is zero or an integer from 1 to about 100 and $R^6$ is a linear or branched alkylene, alkoxyalkylene, cycloalkylene, cycloalkoxyalkylene, arylakylene or aryloxyalkylene residue having 2 to about 20 carbon atoms, with (2) an omega-amino alkylene urea having the formula:

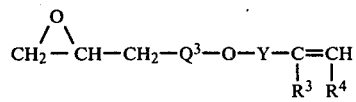

where $R^1$ is alkylene having 2 to 3 carbon atoms;

$R^2$ is alkylene having 2 to about 20 carbon atoms;

$Q^1$ is $(R^5-O)_m$ where m is zero or an integer from 1 to about 100 and $R^5$ is a linear or branched alkylene, alkoxyalkylene, cycloalkylene, cycloalkoxyalkylene, arylakylene or aryloxyalkylene residue having 2 to about 20 carbon atoms, and may be the same as or different from $R^6$ Q$^4$ is $(R^7-O)_p$ where p is zero or an integer from 1 to about 100 and may be the same as or different from m, and $R^7$ is a linear or branched alkylene, alkoxyalkylene, cycloalkylene, cycloalkoxyalkylene, arylalkylene, or aryloxyalkylene residue having 2 to about 20 carbon atoms, and may be the same as or different from $R^5$ and $R^6$ and Q$^6$ is $(R^9-O)_r$ where r is zero or an integer from 1 to about 100 and may be the same as or different from m and p, and $R^9$ is a linear or branched alkylene, alkoxyalkylene, cycloalkylene, cycloalkoxyalkylene, arylalkylene, or aryloxyalkylene residue having 2 to about 20 carbon atoms, and may be the same as or different from $R^5$, $R^6$ and $R^7$, in a molar ratio of from about 0.5 to about 10 moles of unsaturated glycidyl ether or ester per mole of omega-amino alkylene urea and at a temperature in the range of from about 50° C. to about 250° C.

8. A composition of matter according to claim 7 wherein the unsaturated glycidyl ether or ester is an ether having the formula:

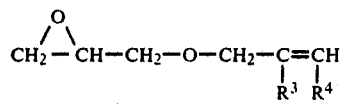

where $R^3$ is H or $CH_3$; and $R^4$ is H or $CH_3$.

9. A composition of matter according to claim 7 wherein the omega-amino alkylene urea has the formula:

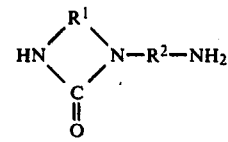

where $R^1$ is alkylene having 2 to 3 carbon atoms; and $R^2$ is alkylene having 2 to about 10 carbon atoms.

10. A composition of matter made by reacting allyl glycidyl ether with 2-aminoethyl ethylene urea in a molar ratio of from about 0.5 to about 10 moles of allyl glycidyl ether per mole of 2-aminoethyl ethylene urea at a temperature of from about 50° C. to about 250° C.

* * * * *

UNITED STATES PATENT AND TRADEMARK OFFICE
CERTIFICATE OF CORRECTION

PATENT NO. : 4,319,032
DATED : March 9, 1982
INVENTOR(S) : JOSEPH M. SANDRI ET AL.

It is certified that error appears in the above—identified patent and that said Letters Patent is hereby corrected as shown below:

Please correct the spelling of co-inventor's name to read --BILLIOUX--.

Column 1, line 25, change "allacrylic" to read --all acrylic--.

Column 25, claim 3, line 45, delete

"$\overset{C}{\underset{O}{|}}$"

Column 26, claim 7, line 65, change "$(R^5-O_m$" to read --$(R^5-O)_m$--.

Column 26, claim 7, line 68, change "lakylene" to read --lalkylene--.

Signed and Sealed this

*Thirteenth* Day of *July 1982*

[SEAL]

*Attest:*

GERALD J. MOSSINGHOFF

*Attesting Officer* — *Commissioner of Patents and Trademarks*